United States Patent [19]
Klotz

[11] Patent Number: 4,719,176
[45] Date of Patent: Jan. 12, 1988

[54] ENZYME-FREE DIAGNOSTIC BINDING REAGENTS

[76] Inventor: Irving M. Klotz, 2515 Pioneer Rd., Evanston, Ill. 60201

[21] Appl. No.: 547,232

[22] Filed: Oct. 31, 1983

[51] Int. Cl.$^4$ .................... C12Q 1/68; G01N 33/566; G01N 33/53; G01N 33/542

[52] U.S. Cl. ........................................ 435/6; 436/501; 436/537; 436/544; 436/547; 436/808; 435/810; 536/27

[58] Field of Search ................ 422/61; 435/6, 810; 436/34, 501, 524, 531, 537, 544, 547; 808/809, 904; 530/387, 402; 536/27

[56] References Cited

U.S. PATENT DOCUMENTS

| | | |
|---|---|---|
| 3,817,837 | 6/1974 | Rubenstein et al. |
| 3,875,011 | 4/1975 | Rubenstein et al. |
| 3,996,345 | 12/1976 | Ullmann et al. |
| 4,160,645 | 7/1979 | Ullman ........................ 436/537 X |
| 4,229,537 | 10/1980 | Hodgins ........................ 435/181 X |
| 4,281,061 | 7/1981 | Zuk ................................ 436/537 X |
| 4,375,972 | 3/1983 | Forgione ............................ 436/531 |
| 4,383,031 | 5/1983 | Boguslaski ....................... 422/61 X |
| 4,535,057 | 8/1985 | Dreesman ...................... 436/548 X |

OTHER PUBLICATIONS

Bender, M. L. *Mechanisms of Homogeneous Catalysis from Protons to Proteins*, Wiley-Interscience, N.Y. 1971, pp. 148–152, 162, 163.

Ikarlyama, Y. et al., *Anal. Chem.* vol. 54, No. 7, 1982, pp. 1126–1129.

Windholz, M. editor, *The Merck Index* 10th edition Merck and Co., Inc. N.J. 1983 p. 671.

Delaney, E. J. et al., *J. Amer. Chem. Soc.*, vol. 104, 1982, pp. 799–807.

Heller, M. J. et al., *J. Amer. Chem. Soc.*, vol. 99, No. 8, 1977, pp. 2780–2785.

Sigel, H., *Angew. Chem. Internat. Edit.* vol. 8, No. 3, 1969, pp. 167–177.

Nango, M. et al., *J. Poly. Sci.* vol. 16, 1978, pp. 1265–1273.

Singer, T. P. et al., *J. Biol. Chem.* vol. 183, 1950, pp. 409–429.

O'Sullivan et al., *Annals of Clinical Biochemistry*, 16, 221–240 (1979).

*Primary Examiner*—Esther M. Kepplinger
*Assistant Examiner*—Jeremy M. Jay
*Attorney, Agent, or Firm*—Dressler, Goldsmith, Shore, Sutker & Milnamow, Ltd.

[57] ABSTRACT

An enzyme-free diagnostic reagent, methods of its use and diagnostic systems containing that reagent are disclosed. The enzyme-free diagnostic reagent comprises an enzyme-free catalyst coupled by a linking group to a first binding agent, binds in aqueous medium to a second binding moiety to form a binding complex, and indicates the amount of second binding moiety present in the complex by means of its catalytic reactivity with co-reactant molecules.

42 Claims, 1 Drawing Figure

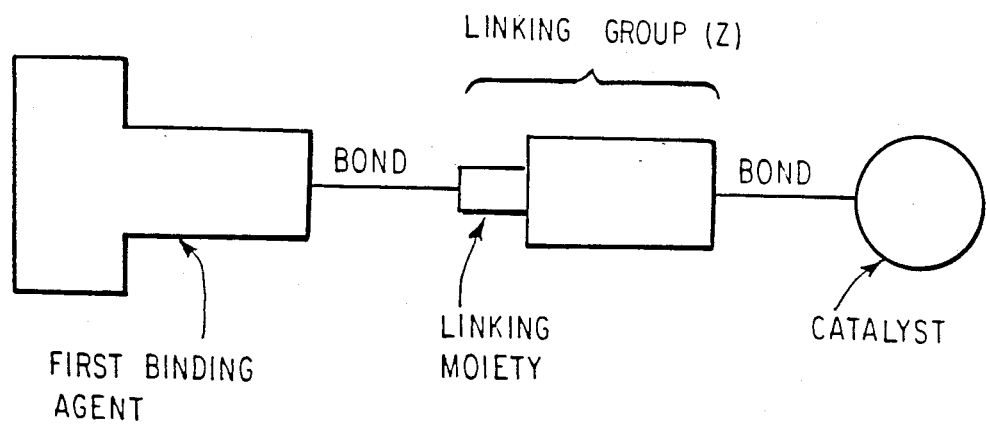

ENZYME-FREE DIAGNOSTIC BINDING REAGENTS

DESCRIPTION

TECHNICAL FIELD

The present invention relates to diagnostic systems, and particularly to binding assay diagnostic reagents that utilize enzyme-free catalysts as labels.

BACKGROUND ART

Binding assays are a frequently used diagnostic tool in the biochemical and medicinal arts. Such assays can provide sensitive probes for determining the presence of small amounts, e.g. nanograms per milliliter, of an entity being assayed.

Binding assays depend upon the interaction or aggregation between two or more entities to form a complex. The presence of the complex is indicated by a label or tag that can be linked to one of the complexed entities or to an exogenously supplied entity that binds to the complex.

One of the most frequently used binding assays is an immunoassay in which one entity is an antigenic protein ligand and the other is a binding reagent such as a receptor comprising an antibody or the idiotype containing portion thereof. The most widely used immunoassay label is a radioisotope [Yalow et al., *Nature*, 184, 1648–1649 (1959)].

However, radioimmunoassays possess a number of disadvantages. For example, the most commonly used radiolabel, iodine-125, is a gamma-emitting isotope with a relatively short shelf-life that usually requires that the labeled diagnostic be prepared within a few days of its use. Radioisotopes also present health hazards in their preparation and use, and are accompanied by the production of radioactive wastes that present an ever increasing problem in disposal. Furthermore, radioimmunoassays require the use of expensive and complicated equipment for quantitative measurement of the amount of binding that has occurred.

These defects in the use of radiolabels have prompted many searches for alternative labels. See, for example, the review and references therein by O'Sullivan et al., *Annals Clinical Biochem.*, 16, 221–240 (1979). The most popular of the alternatives to radiolabels thus far utilized are the enzyme labels.

The properties of enzymes allow them to be used in relatively small quantities because their presence is amplified by the generation of multiple quantities of the product of the reaction catalyzed by the enzyme label. This product or indicia, commonly a colored or fluorescent substance, can typically be detected visually, and its amount can be quantified by relatively inexpensive equipment.

Enzymes, however, are difficult to obtain in high purity, are relatively unstable at elevated temperatures, and are also generally costly. In addition, because of their relatively high molecular weight, e.g. about 20,000 to about 100,000 daltons, and concomitant large bulk, only a few enzyme molecules can typically be bonded per molecule of binding reagent such as an antibody without inhibiting the binding ability of the antibody.

Furthermore, to be used as a label in an immunoassay, enzymes must be conjugated or coupled with the antibody. The coupling reactions necessary to perform that conjugation are, however, not clean-cut due to the multiplicity of reactive sites on both the enzyme and the antibody. Such conjugation reactions typically generate large quantities of undesirable, extraneous contaminants that must be removed or otherwise accounted for to produce an enzyme preparation of high activity.

Thus, it would be beneficial, if a label could be found for binding assays generally, and immunoassays in particular, that is inexpensive to produce, utilizes low cost equipment for making quantitative assay determinations, is stable under a wide variety of temperature and solution conditions, can be conjugated to a binding reagent through one or a few sites of reactivity, and also can be used in relatively small quantities because of an amplification of the assay indicia that it produces.

BRIEF DESCRIPTION OF THE INVENTION

The present invention contemplates an enzyme-free diagnostic reagent that comprises an enzyme-free, chemical catalyst coupled by a linking group to a first binding agent such as a receptor or a ligand. The catalyst (i) has a molecular weight together with the linking group of about 75 to about 2000 daltons, and (ii) catalyzes a chemical reaction with successive molecules of a preselected co-reactant when the co-reactant molecules and catalyst are admixed in an aqueous medium and the catalyst is coupled to a first binding agent as the diagnostic reagent. In particularly preferred practice, the catalyst (iii) is capable of retaining catalytic reactivity after heating anaerobically to a temperature of about 100 degrees C. for a period of about 1 minute when in the absence of the linked first binding agent and in the absence of solvent. The diagnostic reagent containing its coupled catalyst binds in aqueous medium to an unlabeled, second binding moiety to form a binding complex. The diagnostic reagent indicates the amount of binding complex present and thereby the amount of second binding moiety present in the complex by means of its catalytic reactivity with the co-reactant molecules.

Another preferred embodiment of the invention is a diagnostic system that comprises at least one package that contains an aqueous solution including a known amount of the diagnostic reagent of this invention. In more preferred practice, the system further includes at least one additional package that contains a solution of a second known amount of co-reactant molecules for the enzyme-free catalyst of the diagnostic reagent.

The invention further contemplates a method of carrying out a binding assay. Here, the above-described diagnostic reagent is provided, as is a first aqueous composition that contains a second binding moiety. Known, predetermined amounts of the diagnostic reagent and first aqueous composition are admixed in an aqueous medium to form a binding complex between the diagnostic reagent and the second binding moiety. A plurality of co-reactant molecules is admixed with the above admixture, and the reaction between the enzyme-free catalyst and co-reactant molecules is measured. In some assays, the second binding moiety is the entity being assayed. In other assays, the second binding moiety is needed for the assay but the assayed entity is provided by a composition to be assayed that is admixed, preferably in predetermined known amount, with the binding complex-containing aqueous medium prior to admixture of co-reactant molecules.

The present invention provides several benefits and advantages.

One advantage of the present invention is that radioisotopes are not needed as labels in binding assays, and thus the health, waste, and immediacy of use problems associated with radiolabels such as $^{125}$I are avoided.

Another benefit of the present invention is that the catalyst in a form purified for use can be relatively inexpensive as compared to an enzyme preparation of similar purity.

A still further benefit of the present invention is that the enzyme-free catalysts contain one or relatively few sites of reaction for linkage to the first binding agent and thus provide cleaner, higher yield reactions of usable materials after conjugation.

One of the advantages of the present invention is that only small amounts of the catalyst need be utilized because the catalyst amplifies its presence through a plurality of successive reactions with its co-reactant molecules.

Another advantage of the present invention is that the enzyme-free catalysts of this invention are substantially stable when anaerobically heated in the absence of solvent and linked binding reagent as compared to enzyme labels which are not generally stable under similar conditions.

Yet another of the advantages of this invention is that, if desired, more enzyme-free catalyst molecules can be linked per first binding agent molecule than is possible with an enzyme label without affecting the binding and complex forming capabilities of the linked first binding agent because of the relatively small size of the enzyme-free catalysts.

A still further advantage of this invention is that its diagnostic reagents, systems and methods are particularly suited for homogeneous binding assays.

Further benefits and advantages of the present invention will be apparent to those skilled in the art from the detailed description that follows.

BRIEF DESCRIPTION OF THE DRAWING

The sole FIGURE forming a part of this disclosure illustrates a schematic representation of an enzyme-free diagnostic reagent of this invention.

DETAILED DESCRIPTION OF THE INVENTION

A. General Discussion

The present invention contemplates an enzyme-free diagnostic reagent that binds to a second, specific, binding moiety. The diagnostic reagent contains a linked or coupled enzyme-free catalyst that reacts with successive co-reactant molecules to indicate the presence of the diagnostic reagent, and inferentially, the presence of the second binding moiety. The catalytic activity exhibited by the catalyst is utilized for qualitative and/or quantitative determinations for the assayed entity. The enzyme-free catalyst is linked to a first binding agent to form the diagnostic reagent.

The diagnostic reagent of this invention is shown schematically in the sole FIGURE of this invention. In that FIGURE, the first binding agent of the diagnostic reagent is shown, for purposes of clarity, linked to a single catalyst. It is to be understood, however, that an average of about ten or more catalysts may be linked to the first binding agent to form a molecule of the diagnostic reagent as is discussed below. The first binding agent is linked to the linking group, Z, via the linking moiety of the linking group. The linking group is covalently bonded to the enzyme-free catalyst. Exemplary diagnostic reagents, their first binding agents, linking groups, linking moieties and enzyme-free catalysts are discussed in detail hereinafter.

An average of about 1 to about 10 enzyme-free catalysts are preferably coupled per molecule of enzyme-free diagnostic reagent. For heterogeneous binding assays, it is more preferred that the enzyme-free diagnostic reagent contain an average of about 4 to about 7 enzyme-free catalysts linked to the first binding agent to form an enzyme-free diagnostic reagent of this invention. More than about 10 enzyme-free catalysts per diagnostic reagent molecule can also be utilized so long as binding to the substance to be assayed is not substantially impaired. Enzyme-free diagnostic reagents for use in homogeneous binding assays more preferably contain an average of about 1 to about 3 enzyme-free catalysts linked to the first binding agent, as is discussed further hereinafter.

The enzyme-free diagnostic reagents (also sometimes referred to as the "diagnostic reagents") of this invention are preferably water-soluble or water-dispersible. Such preferred materials permit easy usage, particularly in homogeneous assays. It is also contemplated, however, that a diagnostic reagent of this invention may be bound on the surface of an insoluble support such as the walls and bottom of a microtiter plate or upon cross-linked carbohydrate beads or upon glass beads, or the like. When used as insoluble supports, it is important that the enzyme-free diagnostic reagent be sufficiently hydratable to form a binding complex and react with successive co-reactant molecules. Methods of chemically and physically adhering materials such as the diagnostic reagents of this invention to water-insoluble supports are well known in the art, and need not be discussed further herein.

The diagnostic reagents of this invention and the catalysts useful herein are "enzyme-free" in that they contain substantially no naturally occurring or genetically engineered enzymes. Thus, the useful catalysts and the diagnostic reagents of this invention prepared from them are substantially free from enzymes isolated from plant, animal or microbial sources in which enzymes occur in nature, as well as free from enzymes that are produced by genetic engineering techniques by which a gene encoding the enzyme is inserted into a vector which then replicates the gene and expresses the enzymes. The catalysts useful herein are also substantially free from naturally occurring or genetically engineered proteinaceous materials; i.e., polypeptides or glycopolypeptides having a molecular weight of about 10,000 daltons or more.

Useful catalysts may also be termed "synthetic" in that they are man-made. Some of the enzyme-free catalysts useful herein such as 4(5)-chloromethyl imidazole and the 4,4-disubstituted amino pyridines discussed hereinafter are made from their constituent atoms by organic chemical reactions, while others such as heme and riboflavin derivatives may occur in nature, but are man-made in that they are isolated or extracted from their natural sources through human intervention. Such catalysts isolated or extracted from natural sources are also nevertheless enzyme-free and are also substantially free from naturally occurring or genetically engineered proteinaceous materials.

Thus, while trace amounts of naturally occurring or genetically engineered enzymes and/or proteinaceous materials may be present as impurities in a catalyst, the catalyst of this invention is the principal substance that is used as a label or indicator in binding assays, and not such enzymes and/or proteinaceous materials. It is also to be noted that while an enzyme or a proteinaceous material may constitute a part of the enzyme-free diagnostic reagent such as a first binding agent, or constitute a binding agent needed for an assay, reactions catalyzed by an enzyme or proteinaceous material are not the reactions used herein as labels.

The phrase "first binding agent" is used herein for the binding portion of the diagnostic reagent of this invention. The diagnostic reagent also includes an enzyme-free catalyst coupled to the first binding agent, and binds through the binding portion of the first binding agent to at least a second binding moiety.

The phrase "second binding moiety" is used herein to mean the substance that is bound by the enzyme-free diagnostic reagent to form a complex. The second binding moiety is free from a coupled enzyme-free catalyst, and is specifically bound by the diagnostic reagent.

"Specific" binding is to be compared to non-specific binding such as occurs between most proteins and plastic surfaces. Examples of specific binding include that binding between antibody and antigen, avidin and biotin, complementary strands of DNA and/or RNA for each other, protein A of *Staphylococcus aureus* and antibody Fc proteins and the like.

The second binding moiety may be the assayed entity. For example, the second binding moiety is the assayed entity where the enzyme-free diagnostic reagent comprises an antigen linked to a catalyst and an antibody to that antigen is to be assayed by the amount of antigen-antibody complex that is formed upon admixture of the two ingredients.

Alternatively, the second binding moiety may be an entity needed for the assay rather than the assayed entity. For example, the second binding moiety is needed for the assay where a dissociatable complex formed between a small molecule such as a hormone linked to one or more catalysts and an antibody to that hormone is admixed with a composition such as serum to be assayed for the presence of the same hormone. Here, the presence and amount of hormone in the serum are determined indirectly by the difference in observed catalyst reactivity in the absence and presence of the assayed serum. Thus, the anti-hormone antibody that bound to and formed a dissociatable complex with the diagnostic reagent of this invention is not itself assayed, but is "needed" for the assay of the hormone present in the serum.

The word "receptor" as used herein is meant to indicate an antibody or the idiotype-containing polyamide portion of an antibody. Receptors containing a coupled enzyme-free catalyst are one class of particularly preferred enzyme-free diagnostic reagents. Thus, receptors comprise a particularly preferred first binding agent of this invention.

Antibodies or the idiotype-containing polyamide portions of antibodies are biochemically active in that they bind at least with an antigenic ligand when admixed therewith in aqueous solution, at least at physiological pH values and ionic strengths. Preferably, the receptors also bind to the antigenic ligand within a pH value range of about 5 to about 9, and at ionic strengths such as that of distilled water to that of about one molar sodium chloride.

Idiotype-containing polyamide portions of antibodies are the portions of antibodies that bind to an antigen ligand. Such portions include the Fab, Fab', and F(ab')$_2$ fragments prepared from antibodies by well-known enzymatic cleavage techniques.

The receptor molecules can be polyclonal as is the case for the antibodies raised to a whole protein molecule. The receptors can also be oligoclonal such as those that are raised to a polypeptide immunogen as is discussed in Sutcliffe et al., *Science*, 219, 660–666 (1983), and in the articles cited therein.

The receptors can also be monoclonal. Techniques for preparing monoclonal antibodies are well known. Monoclonal receptors useful in this invention can be prepared using a whole protein immunogen, as is customary, or by using a polypeptide as immunogen as described in Niman et al., *Proc. Natl. Acad. Sci. USA*, 80, 4949–4953 (1983). Monoclonal antibodies are typically obtained from hybridoma tissue cultures or from ascites fluid obtained from animals into which the hybridoma tissue was introduced.

The word "receptor" also includes a second antibody or portion thereof that binds to the molecule to be assayed and to which an enzyme-free diagnostic reagent of this invention such as a catalyst-coupled receptor binds. By binding to the molecule to be assayed, the second receptor forms a binding complex whose subsequent binding by the catalyst-coupled receptor provides an indirect means of assaying for the original molecule to be assayed. Thus, the second receptor-assayed molecule complex provides a second binding moiety as defined hereinbefore.

The word "ligand" is used herein to mean an antigenic molecule which binds to and with a receptor. A ligand may be an antigenic protein, an antigenic hapten such as 2,4-dinitrophenol, p-nitrophenol or an antigenic polypeptide having a molecular weight of less than about 6000 daltons such as a hormone.

A ligand may also comprise the first binding agent of a diagnostic reagent of this invention. As discussed in greater detail hereinafter, a polypeptide ligand linked to a catalyst provides another particularly preferred class of diagnostic reagents of this invention.

It is noted that the terms "receptor" and "ligand" are used herein only to describe molecules which form binding complexes of the type that are formed between an antibody and an antigen.

The enzyme-free diagnostic reagent may also be a polynucleic acid such as a DNA or RNA that is complementary in base sequence to and binds with a DNA or RNA second binding moiety. Binding between DNA complementary strands when done on nitrocellulose sheets is frequently referred to as a Southern blot [Southern, *J. Mol. Biol.*, 98, 503–517 (1975)], while similar binding between RNA and DNA molecules is frequently referred to as a Northern blot. [See, for example Milner and Sutcliffe, *Nucleaic Acids Res.*, 11, 5497–5520 (1983).]

Assays for Southern and Northern blots are typically carried out utilizing radioactive labels ($^{32}$P) bonded into polynucleic acid backbone phosphate groups. While such labels have uses in autoradiographic techniques for recording the fact of binding, they suffer from the usual defects of such radioactive materials when used in other types of homogeneous and heterogeneous assays.

Thus, using a so-called "nick" translation, a nucleotide base containing a label such as 2'-deoxyuridine triphosphate 5-allylamine-linked catalyst of this invention can be polymerized into an enzyme-free diagnostic reagent DNA molecule using *E. coli* DNA polymerase 1. The diagnostic reagent so prepared can thereafter be utilized in heterogeneous or homogeneous binding assays.

The first binding agent can also be comprised of a biotin molecule coupled to an enzyme-free catalyst. A diagnostic system utilizing such a diagnostic reagent of this invention can be exemplified in a heterogeneous DNA binding assay.

In one such exemplary assay, the presence and/or amount of a DNA molecule is assayed using a synthesized, complementary strand of DNA to form the binding complex. Here, 2'-deoxyuridine triphosphate 5-alkylamine-biotin (Biotin-11-dUTP; Enzo Biochem, Inc. of New York, NY) is incorporated into a synthesized, complementary DNA molecule by nick translation catalyzed by $E.$ $coli$ DNA polymerase 1. After hybridization (binding complex formation) in an aqueous medium between the synthesized, complementary DNA and the second binding moiety DNA bound on nitrocellulose as in a Southern blot, a soluble complex of strepavidin from $Streptomyces$ $avidinii$ and biotin-coupled enzyme-free catalyst are added to the aqueous medium, followed by addition of co-reactant molecules for the enzyme-free catalyst, as discussed hereinafter.

Thus, the diagnostic system described immediately above encompasses two types of binding: (a) binding between complementary DNA molecules, and (b) biotin-avidin-biotin/catalyst binding of the enzyme-free diagnostic reagent (biotin-catalyst) with the second binding moiety (DNA complex-biotin-avidin) that includes bound molecules of biotin and avidin.

Thus, the present invention relates to biochemical, and particularly immunochemical binding between at least two binding moieties, wherein a catalyst useful herein is bound to one of those moieties to form the enzyme-free diagnostic reagent that is utilized to assay directly or indirectly for the presence of an assayed entity by the formation of a binding complex between the diagnostic reagent and the second binding moiety.

B. Enzyme-Free Catalysts Generally

The enzyme-free catalysts of this invention are relatively small molecules having molecular weights along with their linking groups of about 75 to about 2000 daltons, and more preferably of about 150 to about 1000. Being of relatively low molecular weight, the catalysts useful herein can be designed as to the specificity of their catalytic reaction sites as well as to the number of conjugation-specific sites that each molecule contains. Thus, while a plurality of catalytic reaction sites per catalyst molecule is desirable, one or at most about four sites of coupling or conjugation to the first binding agent are preferred. The present catalysts therefore differ from enzymic labels in which substantially every lysine, serine, threonine, tyrosine, cysteine, glutamic acid and aspartic acid residue, as well as each amino-terminal and/or carboxy-terminal residue on the surface of the enzyme, or at its catalytically active site is a potential position of reaction in coupling reactions such as amide- or ester-forming reactions with the first binding agent.

A particular advantage of the present catalysts and the diagnostic reagents of this invention is that because of their relatively small molecular weight and steric bulk, a relatively large number of catalytic molecules may be conjugated to the first binding agent without substantially interfering with the binding capability of that reagent. For example, several well known enzyme-linked immunoassays utilize intact IgG-type antibodies that have a molecular weight of about 150,000 daltons conjugated to the enzyme horseradish peroxidase (HRP) that has a molecular weight of about 44,000 daltons. It can be readily seen that if one were to link more than a few HRP molecules to an IgG antibody, the steric bulk of the HRP molecules could inhibit the binding capacity of the coupled antibody. On the other hand, when a catalyst and linking group of this invention having a molecular weight of about one twentieth or less of HRP, and a comparably smaller steric bulk, is utilized, more molecules of the enzyme-free catalyst can be linked per antibody molecule without steric inhibition of the binding of that antibody than would be possible in the case of HRP.

A second characteristic of catalysts useful herein is that they catalyze a chemical reaction with successive, preselected co-reactant molecules when those co-reactant molecules and the catalysts are admixed in an aqueous medium and the catalyst is coupled to a first binding agent to form the diagnostic reagent of this invention. This characteristic of the catalyst, also known in the art as "turn over", provides an amplified monitor of the presence of the catalyst so that a large number of catalysts are not needed per molecule of enzyme-free diagnostic reagent.

For example, where a coupled 4,4-disubstituted amino pyridine, discussed hereinafter, is utilized as the catalytic label along with a co-reactant such as p-nitrophenyl caproate, one molecule of the catalyst reacts with a plurality of co-reactant molecules to provide an increased amount of signal, here a yellow color, per catalyst molecule as compared to the amount of gamma radiation signal that is obtained per molecule of a radio-label such as iodine-125, which provides less than one signal per molecule.

The catalysts of the present invention are also further different from proteinacious enzyme labels in that they retain their catalytic activity after being contacted with non-aqueous solvents such as ethanol, acetone, benzene and the like, or with aqueous denaturant compositions such as those containing urea or synthetic detergents like polyoxyethylene (8) nonyl phenyl ether, or $C_{12}$–$C_{20}$ alkyl sulfates, sulfonates or carboxylates and the like.

In particularly preferred practice, the catalysts of the present invention are capable of retaining their catalytic activity when heated anaerobically to a temperature of about 100 degrees C. for a period of about one minute in the absence of the conjugated first binding agent and also in the absence of solvent. Thus, these materials are again different from and superior to typically utilized enzyme labels, which, as protein molecules, suffer denaturation under such conditions.

As noted before, the catalyst useful herein catalyzes a reaction of a co-reactant that is admixed in an aqueous medium with the catalyst-first binding agent conjugate; i.e. the enzyme-free diagnostic reagent. In preferred practice, the reaction catalyzed by the enzyme-free catalyst useful herein is a reaction that generates a spectroscopically observable product such as molecule that absorbs light in the ultraviolet or visible regions, or that emits light as fluorescence or phosphorescence, or that is observable by radiation scattering measurements.

In addition, the reaction catalyzed by the enzyme-free catalyst useful herein may be followed by electrical measurements such as conductivity or potentiometric measurements such as where oxidation-reduction reactions are catalyzed, or through the use of nuclear magnetic residence (NMR) where an NMR-active element such as fluorine-19 or hydrogen-1 originally present in the co-reactant molecule exists in a different magnetic environment after the catalyzed reaction than prior thereto.

The catalysts useful herein are adapted to be used in both homogeneous and heterogeneous assay methods. The previously discussed nucleic acid assay utilizing biotin as the first binding agent of the diagnostic reagent provides one example of a heterogeneous assay method. Exemplary, homogeneous binding assays are discussed hereinafter. Homogeneous binding assays are often preferable to heterogeneous assays because they eliminate time-consuming and error-causing separation steps to remove the label-containing reagent, e.g. the enzyme-free diagnostic reagent of this invention, from the assayed composition, and because homogeneous assays are more amenable to automation.

When utilized in homogeneous assay systems, particularly where substantially intact antibodies comprise the binding portion of the diagnostic reagent, assays for the presence of the assayed substance may be carried out by noting a change, typically a decrease, in the rate at which the enzyme-free catalyst reacts with its co-reactant molecules. Thus, binding complex formation between the enzyme-free diagnostic reagent and the second binding moiety may be used to block at least some of the catalytically reactive sites of the catalyst, thereby slowing or preventing the catalytic reaction that would otherwise occur in the absence of complex formation; i.e., in the absence of the entity being assayed.

While blocking of usual catalytic activity is normally not desirable, it can be useful where a homogeneous assay is to be performed. In such homogeneous assays, a limited number such as an average of about 1 to about 3 enzyme-free catalysts is preferably utilized per molecule of first binding agent to help assure that a decreased reaction rate is observed on binding complex formation.

In one particularly preferred embodiment, a predetermined known amount of dissociatable binding complex is prepared between the first binding agent and second binding moiety present in a first aqueous composition such as between a catalyst-linked antigen such as a hormone and a receptor such as an antibody to that hormone, respectively. The catalyst-linked hormone so used contains an average of about 1 to about 3 catalysts per molecule.

Admixture of the dissociatable complex with a predetermined amount of composition to be assayed that contains the same or homologous epitope-containing hormone (assayed entity) causes dissociation of the binding complex, and binding of at least some of the previously bound antibody to the admixed hormone to form a second binding complex. An amount of the enzyme-free diagnostic reagent that was previously bound to the antibody is thereby freed from the dissociatable binding complex and exhibits the original, per molecule, catalytic activity of that diagnostic regent.

Inasmuch as all of the dissociatable binding complex is typically not dissociatd in such an assay, the catalytic activity exhibited by the thus formed, admixed composition is typically less than that of the per molecule catalytic activity of the enzyme-free diagnostic reagent. Nevertheless, the catalytic activity, measured as the observed rate of reaction, is increased over that exhibited by the diagnostic reagent present in the dissociatable complex. Thus, measurement of the rate of reaction with co-reactant molecules exhibited by the catalyst of the diagnostic reagent when bound in the dissociatable complex and after the assayed composition has been added provides a means for qualitative and quantitative assay. Predetermined, known amounts and concentrations of co-reactant molecules, enzyme-free diagnostic reagent in tne dissociatable complex and assayed composition are utilzed for these assays, following well known scientific practices.

In another embodiment, the enzyme-free catalyst is coupled adjacent to an epitopic region; i.e., the structure bound by a receptor, of an antigen (ligand) having a molecular weight of less than about 6000 daltons. Exemplary of such relatively low molecular weight antigens are hormones and the synthetic polypeptides discussed in Sutcliffe et al., *Science,* 219, 660–666 (1983), and in the references therein. Here, about 1 to about 3 enzyme-free catalysts may be coupled to either or both of the amino- and/or carboxy-terminal residues or between the terminii. Linking the catalysts adjacent to an epitopic region helps to provide at least partial blocking of catalytic activity when the diagnostic reagent is admixed with receptors that bind to the same epitope.

For example, a predetermined, known amount of an enzyme-free diagnostic reagent so formed is provided. That diagnostic reagent is admixed with a composition containing (a) a predetermined, known amount of receptors that bind to both the epitope of the diagnostic reagent and to a homologous epitope of an entity to be assayed, and (b) a first aqueous composition to be assayed for the presence of the assayed entity. When the entity to be assayed is present in the first aqueous composition, that entity and the receptor form a first, dissociatable binding complex. Admixture of the diagnostic reagent causes dissociation of that first binding complex and the formation of a second binding complex between receptors freed from the first, dissociable complex and the diagnostic reagent.

Measurement of the rate of reaction of the catalyst with its co-reactant molecules thereafter provides a means for determining the presence of the assayed entity in the first aqueous composition when that rate is compared to the reaction rate obtained from an aqueous medium containing known, predetermined amounts of the diagnostic reagent and co-reactant molecules, and that is also free from a substance that binds to the diagnostic reagent such as the antibodies of (a), above. Quantitative determination of the amount of second binding moiety may be in a manner analogous to that discussed below.

In yet another embodiment, about 1 to about 3 enzyme-free catalysts are coupled to a receptor such as an idiotype-containing polyamide like an Fab portion of antibody to form the enzyme-free diagnostic reagent. Here, the presence of a relatively high molecular weight second binding moiety such as a protein ligand for the antibody having a molecular weight at least about 20,000 daltons is assayed. It is preferred that the catalyst be coupled adjacent to the idiotypic, binding, region of the receptor so that formation of a binding complex at least partially blocks usual catalytic activity, as discussed hereinabove. A predetermined, known amount of the diagnostic reagent and a first aqueous composition to be assayed for the presence of that second binding moiety (here, the assayed entity) are admixed. A binding complex between the diagnostic reagent and any second binding moiety that is present is formed, and co-reactant molecules are added to the admixture. The rate of the catalytic reaction is then measured.

The rate of reaction exhibited by the admixture is compared to the reaction rate of an aqueous medium containing known, predetermined amounts of the diagnostic reagent and co-reactant molecules and free from a substance that binds to the diagnostic reagent such as the protein second binding moiety. That comparison provides an assessment as to whether the second binding moiety was in fact present in the first aqueous composition. Reaction rates obtained from the use of standard aqueous compositions containing known amounts of the second binding moiety along with predetermined, known amounts of the diagnostic reagent of this invention provide data from which a quantitative determination of the amount of second binding moiety present in the first aqueous composition can be obtained.

In still another embodiment, the present diagnostic reagents may be utilized in a heterogeneous system such as those in which an antigen ligand; i.e., second binding moiety, is bound to a solid substrate such as the walls and bottom of a microtiter well, to which is added a non-assayed protein such as bovine serum albumin to occupy the non-specific binding sites on the microtiter well bottom and walls. Thereafter, a pre-incubated mixture containing (a) catalyst-coupled receptor (diagnostic reagent) that binds to the antigen ligand and (b) a first aqueous composition such as serum that is to be assayed for the presence of the same or homologous antigenic ligand is introduced into the microtiter well. The enzyme-free diagnostic reagent is used in a predetermined, known amount that is in excess of the amount of receptor expected to be present in the known, predetermined amount of first aqueous composition utilized.

Here, the amount of diagnostic reagent receptor in excess of that bound to the antigenic second binding moiety (ligand) in the serum binds to the antigenic ligand previously bound to the walls and bottom of the microtiter well to form a heterogenous composition. Rinsing of the microtiter well removes diagnostic reagent not bound to the microtiter well, and is followed by introduction of suitable co-reactant molecules to provide an indirect assay of the presence and amount of the assayed antigen ligand (second binding moiety).

Broadly, then, the method of carrying out a binding assay in accordance with this invention is as follows. An enzyme-free diagnostic reagent of this invention is provided, as is a first aqueous composition that contains a second binding moiety. Known, predetermined amounts of the diagnostic reagent and the first aqueous composition are admixed in an aqueous medium to form a binding complex between the diagnostic reagent and the second binding moiety. A plurality of co-reactant molecules for the enzyme-free catalyst are admixed with the binding complex-containing aqueous medium of the above admixture. The reaction between the enzyme-free catalyst and co-reactant molecules is then measured to indicate the presence and/or amount of second binding moiety. Where the second binding moiety is an entity needed for the assay, rather than the assayed entity, a composition to be assayed is admixed with the aqueous medium containing the binding complex prior to admixture of co-reactant molecules.

The aqueous medium utilized for the above admixture and complex formation may be a water solution, a buffered or unbuffered composition, serum or plasma, saliva, urine, a tissue section to which the diagnostic reagent in water is applied, or the like. The important feature of the aqueous medium is that that medium wet the diagnostic reagent and second binding moiety sufficiently so that a binding complex may form.

C. Specific Catalysts

Specific catalysts useful herein include the following that are intended to be exemplary of such catalysts, and not limiting.

1. Hydrolytic Catalysts

A preferred group of hydrolytic catalysts are the 4-substituted amino pyridine derivatives such as the particularly preferred 3-[methyl(4-pyridyl)amino] propionic acid having the structure shown below in formula I:

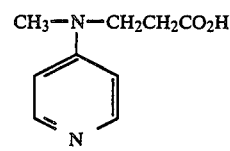

Materials such as that of formula I constitute members of a broader group of 4-substituted amino pyridines having a structure corresponding to that shown in formula II:

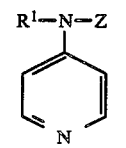

wherein $R^1$ is hydrogen, $C_1$–$C_{12}$ alkyl, or Z; and

Z is a linking group containing a linking moiety; or where $R^1$ and Z together form a 5- or 6-membered ring that contains a linking moiety. Linking groups and linking moieties are discussed hereinafter.

Further compounds exemplary of those of formula II include the compounds disclosed in Delaney, Wood and Klotz, J. Am. Chem. Soc., 104, 799–807 (1982), whose disclosures are incorporated herein by reference.

Another useful group of hydrolytic catalysts are 4(5)-substituted imidazoles wherein the 4(5)-substitutent is the linking group that contains the linking moiety, as discussed hereinafter. The useful imidazoles conform in structure to that shown in formula III:

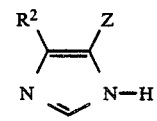

wherein $R^2$ is hydrogen or $C_1$–$C_4$ alkyl and Z is a linking group. Exemplary of such imidazole derivatives are histamine, 4(5)-chloromethylimidazole and imidazole acetic acid.

Additional illustrative examples of useful catalysts whose structures correspond generally to formula III are histidine-containing polypeptides that include about 3 to about 40, and preferably about 4 to about 15, amino acid residues. An illustrative catalyst has an amino acid residue sequence that corresponds to a formula (III-a, -b and -c), from left to right and in the direction of amino-terminus to carboxy-terminus, selected from the group consisting of III-a: N-Acetyl-Gly-Arg-Phe-Cys-Phe-His-Gly;
III-b: N-Acetyl-His-Pro-Cys-Pro-His-Gly; and
III-c: N-Acetyl-Cys-Gly-His-Gly.

The linking group Z in the above formulas thus constitutes all of the polypeptide chain exclusive of the imidazyl group. Such polypeptides may be linked to the first binding agent as discussed hereinafter by means of a linking moiety such as the amine of the amino-terminus or the carboxylic acid of the carboxy-terminus, or by another reactive moiety such as a sulfur of a cysteine residue within the polypeptide chain. When the amino-terminal amine moiety is not utilized as the linking moiety, it is preferred that it be blocked, as by amide formation to prevent a hydrolytic reaction caused by such terminal primary amine. Useful histidine-containing polypeptides such as those above can be prepared as discussed in Heller, Walder and Klotz, J. Am. Chem. Soc., 99, 2780–2785 (1977), whose disclosures are incorporated herein by reference.

Yet another group of useful hydrolytic catalysts are nucelophilic, aliphatic tertiary amines that have $pK_a$ values, measured as acid salts, in excess of about 9 and that have a structure that conforms generally to that of formula IV

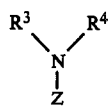

IV wherein Z is as before defined, $R^3$ is $C_1-C_4$ alkyl, and $R^4$ is an alkyl or substituted arylalkyl containing 1 to about 18 carbon atoms; or two of $R^3$, $R^4$ and Z taken together form a 5- or 6-membered ring containing a linking moiety; or, $R^3$, $R^4$ and Z taken together form a bicyclic ring compound containing a linking moiety, each of the rings of the bicyclic ring compound containing 5- or 6-members.

Exemplary compounds whose structures conform to formula IV wherein $R^3$, $R^4$ and Z are separate entities that are not taken together to form one or more rings, include 3-N-methyl-3-N-laurylaminopropionic acid, N,N-dimethylglycine, 3-(dimethylamino)propylamine, 3-(dimethylamino)propionaldehyde, and the like. Exemplary compounds whose structures conform to formula IV wherein $R^3$ and $R^4$ together form 5- or 6-membered rings include N-carboxyethyl pyrrolidine and 3-(1-piperidyl)propionaldehyde. Illustrative of compounds wherein $R^3$ and Z, or $R^4$ and Z taken together form a 5- or 6-membered ring include 1-methyl-3-pyrrolidinol and 1-lauryl-2-piperidinecarboxylic acid. 3-Quinuclidinone is exemplary of compounds wherein $R^3$, $R^4$ and Z taken together form a bicylic ring compound each whose rings contains 5- or 6-members.

Hydrolytic catalytic indicators are utilized with hydrolyzable co-reactant molecules. An exemplary co-reactant for the beforedescribed catalysts is p-nitrophenyl caproate, which upon hydrolysis yields p-nitrophenol that exhibits a yellow color in aqueous media having pH values in excess of about 7. In preferred practice, color-forming, hydrolyzable co-reactants are utilized with the beforedescribed catalysts in aqueous media having pH values of about 7 to about 9.5, as is discussed above in Delaney, Wood and Klotz; Johnson and Klotz hereinafter; and in Nango and Klotz, J. Poly. Sci., 16, 1265–1273 (1978), whose disclosures are incorporated herein by reference.

2. Oxidation-Reduction Catalysts

Another group of useful catalytic labels are catalysts that promote oxidation and reduction (redox) reactions. For example, the aerobic oxidation reaction of dihydronicotinamide adenine dinucleotide (NADH) to its oxidized form nicotinamide adenine dinucleotide (NAD) has been shown to be catalyzed by riboflavin. [Singer and Kearney, J. Biol. Chem., 183, 409–429 (1950)]. The oxidation of NADH to NAD can be followed spectrophotometrically at a wavelength of 340 nanometers by the changes in absorbances of the respective molecules. Riboflavin derivatives that catalyze the aerobic NADA to NAD reaction constitute another group of enzyme-free catalysts useful herein.

Riboflavin derivatives useful herein correspond in structure to that shown in formula V, below

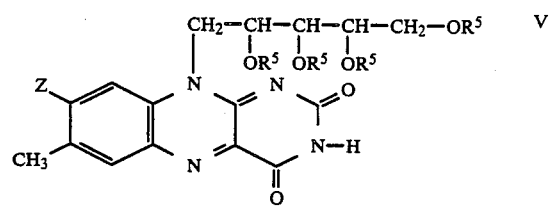

wherein Z is as described before and each $R^5$ is independently selected from the group consisting of hydrogen, $C_1-C_4$ alkyl and $C_1-C_3$ acyl.

A specific, preferred useful riboflavin is alpha-bromo-2',3',4',5'-tetracetylriboflavin which can be linked via its alpha-bromo group to an amino group of the first binding agent following the general techniques discussed in Spetnagel and Klotz, Biopolymers, 17, 1657–1668 (1978), whose disclosures are incorporated herein by reference. That paper also discloses additional useful riboflavins.

Another class of oxidation-reduction catalysts are the iron-porphyrin compounds such as those discussed by Lemberg and Legge, Hematin Compounds and Bile Pigments, Interscience Publishers, Inc., New York (1949), pages 402–403. These redox catalysts have peroxidase-like activities, and in the presence of hydrogen peroxide and well known oxidation-reduction dye precursor co-reactants such as diaminobenzidine cause the formation of colored materials whose concentration can be measured spectrophotometrically.

Iron-porphyrins are another class of preferred oxidation-reduction catalysts, and correspond generally to the structure shown in general formula VI:

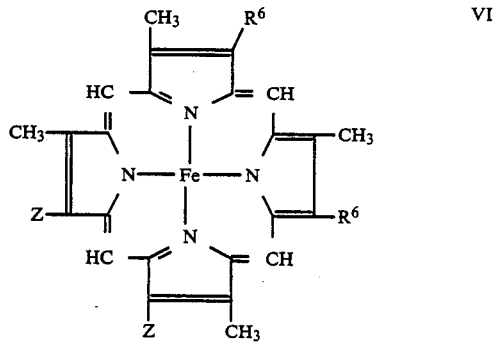

wherein Z is as described before, each $R^6$ is independently $C_1$-$C_4$ alkyl or $C_2$-$C_4$ alkenyl and Fe has an oxidation state of +2 or +3. A particularly preferred iron-porphyrin is heme, also known as ferroprotoporphyrin, whose structure conforms to formula VII, below.

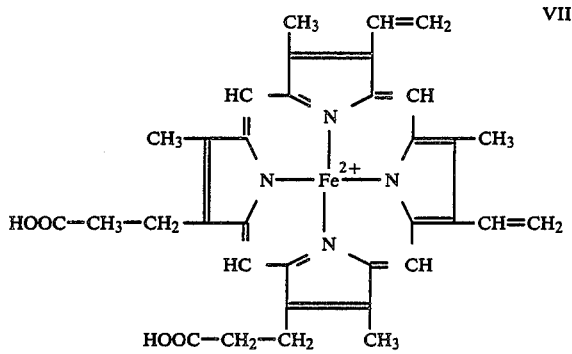

Another class of useful oxidation-reduction catalysts are amine-containing co-ordination complexes containing the iron (II) ($Fe^{+2}$) or copper (II) ($Cu^{+2}$) ion that have catalase-like activity in decomposing hydrogen peroxide. Such materials are described in Sigel, *Angew Chem. Internat. Ed.*, 8, 167–177 (1969), and Wang, *J. Am. Chem. Soc.*, 77, 822–823 (1955), both of whose disclosures are incorporated herein by reference. These co-ordination-complex catalysts typically have a five-membered ring structure, and generally conform to the structure shown in formula VIII, below

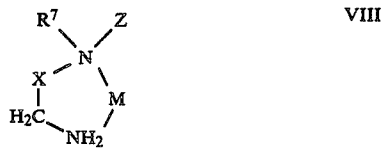

wherein Z is as described before; X is —CH—$_2$ or C=O; $R^7$ is hydrogen or is absent when X is C=O (carbonyl); M is $Cu^{+2}$ or $Fe^{+2}$, and dotted lines represent co-ordination bonds.

Specific examples of catalysts whose structures correspond to structure of formula VIII include the complexes formed between copper (II) and glycylglycine, 1,5-diaminopentane diglycinamide [$NH_2CH_2CONH(CH_2)_5NHCOCH_2NH_2$] or ethylenediaminemonoacetic acid, and those formed between iron (II) and triethylenetetramine.

D. Linking Groups

The linking group, Z, contains a linking moiety that reacts with the first binding agent. The linking moiety is typically a reactive group such as an amine, a carboxylic acid, a mercaptan, an oxo such as ketone or aldehyde, or an activated halomethyl such as the chloromethyl group of 4(5)-chloromethylimidazole. Each of the linking moieties reacts with an appropriate reactive group of a first binding agent to form a covalent bond that links the catalyst to the first binding agent to form the enzyme-free diagnostic reagent of this invention.

It is to be understood that once the linking moiety reacts and couples with the first binding agent, the linking moiety no longer exists as it was prior to that reaction. For example, once a primary amine linking moiety reacts with the carboxyl group of an antibody first binding agent, the nitrogen atom of the primary amino group becomes the nitrogen atom of an amide bond. Thus, the above-discussed catalysts conform to the structures of formulas I through VIII prior to their linking to form a diagnostic reagent of this invention.

Linking groups preferably contain a total of about 1 to about 60 carbon atoms, including the linking moiety, and are preferably alkyl or substituted alkyl, but may also include aryl, substituted aryl and arylalkyl. More preferably, the linking group contains about 1 to about 10 carbon atoms. Linking groups bonded to hydrolytic catalysts are free from electron withdrawing groups such as carbonyl or phenyl groups bonded directly to the nucleophilic atom of the hydrolytic catalyst, e.g. a nitrogen atom, as such electron withdrawing groups diminish the reactivity of the catalyst.

Exemplary linking groups that may be utilized include carboxylic acid-containing alkyl or arylalkyl groups such as 3-carboxyethyl, 4-carboxybenzyl, and 9-carboxynonyl. Carboxylic acid-containing linking groups may be bonded to the first binding agent by the formation of amide, ester or thioester bonds therewith. Such bond formation can be assisted by the use of the acid in ester form such as a methyl ester. Activation of the acid carboxyl group for linking can also be accomplished through the use of a carbodiimide reagent such as 1-ethyl-3-(3-dimethylamino)propyl carbodiimide as disclosed by Hierl, Gamson and Klotz, *J. Am. Chem. Soc.*, 101, 6020–6022 (1979), whose disclosures are incorporated herein by reference.

Additional linking groups include 2-hydroxy-3-chloropropyl or 2,3-epoxypropyl which may be obtained by the reaction of epichlorohydrin with an amino group of the catalyst such as the 4-amino group of an unsubstituted or mono-substituted 4-amino pyridine. Well known base or acid catalyzed reactions, respectively, may be used to link the linking group bonded catalyst to the first binding agent.

Aldehyde- or ketone-containing linking groups may also be used. Exemplary of such linking groups are the 3-oxopropyl group and the 3-oxobutyl group which may be bonded to an amine of the catalyst such as a mono-substituted 4-amino pyridine like 4-methylamino pyridine via the Michael addition of acrolein or methyl vinyl ketone, respectively, to the 4-methylamino moiety of the molecule. Aldehyde- and ketone-containing linking groups may thereafter be coupled to an amino group of a first binding agent by reductive alkylation techniques such as those discussed in Johnson and Klotz, *Macromolecules*, 7, 149–153 (1974), whose disclosures are also incorporated herein.

Amine-containing linking groups are also useful. Such linking groups may be added to the catalyst molecule by the well-known ring-opening reaction between aziridine and an amine of the catalyst such as 4-ethylamino pyridine.

An amine-containing linking group may also be added to the catalyst by the reaction of N-2-bromoethyl maleimide or phthalimide with the 4-amino group of 4-amino pyridine. The imide moieties of such reaction products may be conveniently removed by the method of Sheehan and Frank, *J. Am. Chem. Soc.*, 71, 1856–1861 (1949) to leave a free primary amine linking moiety.

Amine-containing linking groups can also be bonded to an amine-containing first binding agent by means of a di-aldehyde such as glutaraldehyde, as is frequently used for conjugations of various molecules to proteins.

Use of the above-mentioned carbodiimide with a primary- or secondary amine-containing linking moiety of a linking group and a protein first binding agent assists in forming an amide bond with a carboxylic acid of an amino acid residue of the first binding agent.

A catalyst useful herein can also first be bonded to a multivalent radical that is subsequently bonded to the first binding agent. The use of such multivalent radicals provides a means for coupling a relatively large number of enzyme-free catalysts per molecule of the diagnostic reagent. Thus, such multivalent radicals provide a larger linking group, and multivalent radicals together with one or more linking groups already present and bonded to the catalyst are considered together as a single linking group. Thus, the diagnostic reagent of this invention may include a multivalent radical bonded to a plurality of catalysts. In some instances the presence of a multivalent radical can also enhance the catalytic reactivity of the catalyst.

Polymeric polyamines provide one illustrative group of multivalent radicals. Polyethyleneimine (PEI) is exemplary of a useful polymeric polyamine-containing multivalent radical, and may be classified herein as a substituted alkyl linking group. This polymer is a branched, enzyme-free material described by its manufacturer (Dow Chemical Co., Midland, MI) as containing about 25 percent primary amines, about 50 percent secondary amines and about 25 percent tertiary amines. PEI is available commercially in average molecular weights of about 600, 1800, and 60,000.

Unsubstituted PEI may be utilized, or PEI substituted with about 5 to about 15 mole percent (based on nitrogen atoms) $C_{12}$-$C_{18}$ alkyl such as lauryl may be used with one or a plurality of coupled catalysts. Catalyst-coupled PEI or catalyst-coupled $C_{12}$-$C_{18}$ alkyl substituted PEI can be linked through a PEI-amine to a first binding agent using the beforedescribed carbodiimide, or via a further reaction with an additional linking group such as glutaraldehyde also described before.

When polymeric polyamine-containing multivalent radicals are utilized, it is preferred that any primary amines be blocked by the formation of amide groups as by reaction with acetic anhydride, or by the formation of secondary amines as by a reductive alkylation using a ketone such as acetone and a reducing agent such as sodium borohydride as described in Johnson and Klotz, above. It is also noted that although PEI contains tertiary amines, those amines are less effective in catalyzing hydrolytic reactions than are tertiary amines of this invention that correspond in structure to formula IV.

Another useful multivalent radical is s-triazinyl which is typically derived from 2,4,6-trichloro-s-triazine. The trichloro-s-triazine may be used to form an intermediate containing two molecules of coupled catalyst. The intermediate so formed may then be coupled to an amine group such as an epsilon-amino group of a lysine or an amino-terminal primary amine of an amino acid residue of a first binding agent such as a receptor to form the triazinyl radical, following the general techniques of Nango, Gamson and Klotz, J. Poly. Sci., 17, 1557–1563 (1979), whose disclosures are incorporated herein by reference. The two catalyst-containing intermediate can also first be reacted with a diamine such as 1,6-diaminohexane or an amino acid such as epsilon-amino caproic acid and the product of that reaction linked to a first binding agent as described before.

E. Exemplary Enzyme-Free Catalyst-Containing Receptor

The following preparation is exemplary of a useful synthesis for linking a useful catalyst to a first binding agent such as an antibody receptor to form an enzyme-free diagnostic reagent of this invention. This method is also applicable to linking of a catalyst to an antigen ligand, a hapten and the like. Methods of raising antibodies that bind to specific antigens are well known in the art and will not be dealt with further herein. In addition, antibodies from one animal species raised to the Fc portions of antibodies of another species, such as goat anti-rabbit antibodies, are commercially available.

Equimolar amounts of a catalyst of this invention such as 3-[methyl(4-pyridyl)amino]propionic acid and 1-ethyl-3-(3-dimethylamino)propyl carbodiimide are admixed with the antibody in water solution at a pH value of about 6. The ratio of catalyst to protein is in the range of about 10 to about 30 micrograms of catalyst, including the linking group, per milligram of antibody, with an antibody concentration of about 10 to about 20 milligrams per milliliter of reaction solution.

The admixture is permitted to react with gentle agitation for a period of about 1 to about 10 days. The amount of reaction may be followed by use of silica gel thin layer chromatography with methanol as solvent.

Upon completion of the reaction, the catalyst- coupled antibody (diagnostic reagent) is purified as desired by dialysis, or ultrafiltration with an Amicon DIAFLO (Amicon Corp. Danvers, Mass.) stirred ultrafiltration vessel or by immunosorbent chromatography using the immunogen used to raise the antibody bound to a sorbent such as SEPHAROSE 4B (Pharmacia Fine Chemicals, Piscataway, N.J.). The catalyst-coupled antibody solution may then be adjusted to a desired volume, and used from the aqueous medium, or that medium can be freeze dried for later use of the linked catalyst after re-dissolution.

Linking reactions of the useful catalysts to polynucleic acids can be carried out using well-known techniques such as nick translation using a 2'-deoxyuridine triphosphate 5-allylamine-catalyst following the general procedures discussed in Langer et al., Proc. Natl. Acad. Sci. U.S.A., 78, 6633–6637 (1981).

F. Diagnostic Kits

The enzyme-free diagnostic reagents of this invention are designed to be used alone with their co-reactant molecules. However, the principal commercial embodiment of these diagnostic reagents is believed to be as a diagnostic system, preferably in the form of a kit, that contains at least an aqueous solution including a known amount of a diagnostic reagent of this invention in a package such as a bottle. The diagnostic system preferably also further includes at least one additional package that contains a solution of a second known concentration of appropriate co-reactant molecules for the enzyme-free catalyst. Additional, separate packages are utilized when more than one co-reactant is used such as hydrogen peroxide and an oxidation dye precursor.

An exemplary kit for heterogeneous binding assays includes a bottle that contains an aqueous solution of the enzyme-free diagnostic reagent of this invention. An exemplary diagnostic reagent comprises an intact goat anti-rabbit IgG antibody as a first binding agent that is coupled via an amide bond to a 3-[methyl(4-pyridyl)amino]-propionic acid, as catalyst, through the above named carboxylic acid linking moiety. Also included in the kit is a bottle that contains a p-nitrophenyl caproate co-reactant molecules dissolved at a second known concentration in a water-miscible substantially dry solvent such as acetonitrile.

A microtiter plate such as a Falcon 96-well plate as is available from Fisher Scientific Company (Pittsburg, PA.) can also be included with the kit where the binding assay is a heterogeneous assay. Such plates provide surfaces to which proteinaceous materials can bind as has already been discussed.

An exemplary heterogeneous binding assay of the so-called sandwich type is carried out as follows. A known amount of protein ligand such as inactivated influenza virus is bound to the walls and bottom of the microtiter plate followed by an aliquot of another protein such as bovine serum albumin to block non-specific binding sites on the microtiter plates.

Thereafter, a preselected, known amount of a first aqueous composition such as serum to be analyzed for the presence of an influenza virus ligand such as the hemagglutinin molecule is incubated in an aqueous medium with a known, but excess amount of rabbit anti-influenza serum. The incubated composition is then added to the microtiter wells containing previously bound, inactivated influenza virus so that any rabbit anti-influenza antibody in excess of the influenza ligand present in the analyzed sample binds to the previously bound, inactivated influenza on the walls and bottom of the microtiter plate wells. The microtiter plate is thereafter rinsed of excess, unbound materials.

The exemplary catalyst-coupled goat anti-rabbit antibody is added in predetermined, known amount to the rinsed microtiter plate to bind to any bound rabbit anti-influenza antibodies. The microtiter plate is rinsed again to remove unbound catalyst-coupled goat anti-rabbit antibodies. A known amount of the co-reactant p-nitrophenyl caproate is added in a buffer solution such as 0.01 molar sodium borate having a pH value of about 9.2. The absorbance at 400 nanometers is measured spectrophotometrically and corrected for the intrinsic, small amount of hydrolysis of p-nitrophenyl caproate in buffer alone to obtain a quantitative measurement of the amount of catalyst-coupled goat anti-rabbit antibody bound to the microtiter plate and thereby the amount of influenza present in the assayed sample.

The foregoing is intended as illustrative of the present invention but not limiting. Numerous variations and modifications may be effected without departing from the true spirit and scope of the novel concepts of the invention.

What is claimed is:

1. An enzyme-free diagnostic reagent for determining the presence of an entity to be assayed in a homogeneous assay comprising an enzyme-free hydrolytic catalyst coupled by a linking group to a first binding agent, said catalyst having a molecular weight together with the linking group of about 75 to about 2000 daltons, wherein said catalyst catalyzes a hydrolytic chemical reaction with successive preselected hydrolyzable co-reactant molecules when said co-reactant molecules and said catalyst are admixed in homogenous solution and said catalyst is coupled to said first binding agent as said diagnostic reagent; said diagnostic reagent specifically binding in aqueous medium to a second binding moiety to form a binding complex, said second binding moiety being (a) the entity to be assayed in a direct assay, or (b) an entity needed for the assay in an indirect assay, said diagnostic reagent indicating the amount of said second binding moiety present in said binding complex by means of the catalytic reactivity of said catalyst with said co-reactant molecules, said catalytic reactivity being changed when said binding complex is formed.

2. The enzyme-free diagnostic reagent of claim 1 wherein said enzyme-free hydrolytic catalyst has a molecular weight of about 150 to 1000 daltons, and prior to being coupled to said first binding agent has a structure corresponding to a formula selected from the group consisting of

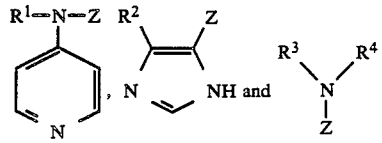

wherein $R^1$ is hydrogen, $C_1$–$C_{12}$ alkyl or Z, or $R^1$ and Z taken together form a 5- or 6-membered ring that contains a linking moiety;

$R^2$ is hydrogen or $C_1$–$C_4$ alkyl;

$R^3$ is $C_1$–$C_4$ alkyl, and $R^4$ is alkyl or substituted arylalkyl containing 1 to about 18 carbon atoms, or two of $R^3$, $R^4$ and Z taken together form a 5- or 6-membered ring containing a linking moiety, or $R^3$, $R^4$ and Z taken together form a bicyclic ring compound containing a linking moiety and wherein each of the rings of the bicyclic ring compound contains 5- or 6-membered ring that contains a linking moiety; and Z is a linking group including a linking moiety prior to linking of the catalyst to the first binding agent.

3. The enzyme-free diagnostic reagent of claim 1 wherein an average of about 1 to about 10 enzyme-free catalysts are coupled per molecule of said enzyme-free diagnostic reagent.

4. The enzyme-free diagnostic reagent of claim 1 wherein said first binding agent is a receptor.

5. The enzyme-free diagnostic reagent of claim 1 wherein said first binding agent comprises a receptor that is an antibody or an idiotype-containing polyamide portion of an antibody.

6. The enzyme-free diagnostic reagent of claim 1 wherein said first binding agent comprises biotin.

7. The enzyme-free diagnostic reagent of claim 1 wherein said first binding agent comprises a polynucleic acid.

8. The enzyme-free diagnostic reagent of claim 1 wherein said first binding agent comprises a ligand.

9. The enzyme-free diagnostic reagent of claim 1 wherein said first binding agent is a ligand.

10. The enzyme-free diagnostic reagent of claim 1 wherein said first binding agent includes avidin bound thereto.

11. The enzyme-free diagnostic reagent of claim 1 wherein said first binding agent comprises a polynucleic acid.

12. The enzyme-free diagnostic reagent of claim 1 wherein said enzyme-free catalyst is coupled adjacent to an epitopic region of a first binding agent that is an antigen having a molecular weight of less than about 6000 daltons, and an average per 1 to about 3 coupled catalysts are present per molecule of said antigen.

13. The enzyme-free diagnostic reagent of claim 1 wherein said enzyme-free catalyst is coupled adjacent to the idiotypic region of a receptor as first binding agent, said receptor being an antibody or the idiotype-containing polyamide portion of an antibody, and an average of about 1 to about 3 coupled catalysts are present per molecule of said receptor.

14. The enzyme-free diagnostic reagent of claim 1 wherein said linking group includes a multivalent radical bonded to a plurality of catalysts.

15. The enzyme-free diagnostic reagent of claim 1 wherein said multivalent radical is selected from the group consisting of a polymeric polyamine and s-triazinyl.

16. The enzyme-free diagnostic reagent of claim 1 wherein said catalyst is additionally capable of retaining catalytic reactivity in the absence of both said coupled first binding agent and solvent, after heating anaerobically to a temperature of about 100 degrees C. for a period of about one minute.

17. A diagnostic kit comprising at least one package containing an aqueous solution including a known amount of an enzyme-free diagnostic reagent for determining the presence of an entity to be assayed in a homogeneous assay, said diagnostic reagent comprising an enzyme-free hydrolytic catalyst coupled by a linking group to a first binding agent, said catalyst having a molecular weight together with the linking group of about 75 to about 2000 daltons, wherein said catalyst catalyzes a hydrolytic chemical reaction with successive preselected hyrolyzable co-reactant molecules when said co-reactant molecules and said catalyst are admixed in homogeneous solution and said catalyst is coupled to said first binding agent as said diagnostic reagent; said diagnostic reagent specifically binding in aqueous medium to a second binding moiety to form a binding complex, said second binding moiety being (a) the entity to be assayed in a direct assay, or (b) an entity needed for the assay in an indirect assay, said diagnostic reagent indicating the amount of said second binding moiety present in said binding complex by means of the catalytic reactivity of said catalyst with said co-reactant molecules, said catalytic reactivity being changed when said binding complex is formed.

18. The diagnostic kit of claim 17 further including at least one additional package that contains a solution of a second known concentration of hydrolyzable co-reactant molecules for said enzyme-free catalyst.

19. A method of carrying out a binding assay comprising the steps of
(a) providing an enzyme-free diagnostic reagent for determining the presence of an entity to be assayed in a homogeneous assay comprising an enzyme-free hydrolytic catalyst coupled by a linking group to a first binding agent, said catalyst having a molecular weight together with the linking group of about 75 to about 2000 daltons, wherein said catalyst catalyzes a hydrolytic chemical reaction with successive preselected hydrolyzable co-reactant molecules when said co-reactant molecules and said catalyst are admixed. in homogeneous solution and said catalyst is coupled to said first binding agent as said diagnostic reagent; said diagnostic reagent specifically binding in aqueous medium to a second binding moiety to form a binding complex, said second binding moiety being (a) the entity to be assayed in a direct assay, or (b) an entity needed for the assay in an indirect assay, said diagnostic reagent indicating the amount of said second binding moiety present in said binding complex by means of the catalytic reactivity of said catalyst with said co-reactant molecules, said catalytic reactivity being changed when said binding complex is formed;
(b) providing a first aqueous composition containing said second binding moiety;
(c) admixing in an aqueous medium a known, predetermined amount of said diagnostic reagent and a known, predetermined amount of said first aqueous composition to form a binding complex between said diagnostic reagent and said second binding moiety;
(d) admixing a plurality of hydrolyzable co-reactant molecules with the admixture of step (c); and
(e) measuring the reaction between said enzyme-free catalyst and said co-reactant molecules.

20. The method of claim 19 wherein said second binding moiety is the entity to be assayed.

21. The method of claim 19 wherein said second binding moiety is needed for the assay and the entity to be assayed is provided by admixing a composition to be assayed with said binding complex-containing aqueous medium prior to said admixture of co-reactant molecules.

22. The method of claim 19 wherein said enzyme-free hydrolytic catalyst has a molecular weight of about 150 to about 1000 daltons, and prior to being coupled to said first binding agent has a structure corresponding to a formula selected from the group consisting of

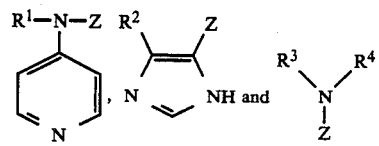

wherein $R^1$ is hydrogen, $C_1$–$C_{12}$ alkyl or Z, or $R^1$ and Z taken together form a 5- or 6- membered ring that contains a linking moiety;
$R^2$ is hydrogen or $C_1$–$C_4$ alkyl;
$R^3$ is $C_1$–$C_4$ alkyl, and $R^4$ is alkyl or substituted arylalkyl containing 1 to about 18 carbon atoms, or two of $R^3$, $R^4$ and Z taken together form a 5- or 6-membered ring containing a linking moiety, or $R^3$, $R^4$ and Z taken together form a bicyclic ring compound containing a linking moiety and wherein each of the rings of the bicyclic ring compound contains 5- or 6-membered ring that contains a linking moiety; and
Z is a linking group including a linking moiety prior to linking of the catalyst to the first binding agent.

23. The method of claim 19 wherein said diagnostic reagent contains an average of about 1 to about 3 catalysts per molecule.

24. The method of claim 23 wherein
(a) said diagnostic reagent comprises said enzyme-free catalyst coupled adjacent to the epitopic region of an antigen having a molecular weight of less than about 6000;
(b) said diagnostic reagent is admixed with a composition containing
(i) a predetermined, known amount of receptors that bind to both the epitope of said diagnostic reagent and to a homologous epitope of an entity to be assayed; and
(ii) a first aqueous composition to be assayed for the presence of the entity to be assayed;

(c) the rate of reaction between said catalyst of said diagnostic reagent in the admixture so formed and said co-reactant molecules is measured; and (d) said measured rate is compared to the rate of reaction of an aqueous medium containing a known, predetermined amount of said diagnostic reagent and co-reactant molecules and free from a substance that binds to said diagnostic reagent.

25. The method of claim 23 wherein (a) said diagnostic reagent comprises said enzyme-free catalyst coupled to an antigen;

(b) said second binding moiety comprises a receptor that binds to and forms a dissociatable binding complex with sid diagnostic reagent;

(c) a predetermined known amount of said dissociatable binding complex is formed in an aqueous medium between said diagnostic reagent and said second binding moiety;

(d) prior to admixture of said co-reactant molecules, a predetermined, known amount of a composition to be assayed that contains the same or a homologous epitope-containing antigen as the assayed entity is admixed with said dissociatable complex, said admixture dissociating said first-named complex, forming a second binding complex between the assayed entity and said receptor, and freeing at least some of said diagnostic reagent previously bound to said receptor in said dissociatable complex; and (e) said co-reactant molecules are thereafter admixed, and said reaction rate is measured and compared to the reaction rate exhibited by said catalyst in said dissociatable complex.

26. The method of claim 23 wherein (a) said diagnostic reagent comprises as the first binding agent a receptor that binds to said second binding moiety, and said catalyst is coupled adjacent to the idiotypic region of said receptor;

(b) said second binding moiety is a protein ligand having a molecular weight of at least about 20,000 daltons; and (c) said measured rate is compared to the rate of reaction of an aqueous medium containing a known, predetermined amount of said diagnostic regent and co-reactant molecules and free from a substance that is bound by said antibody first binding agent.

27. The method of claim 26 wherein said receptor is an idiotype-containing polyamide.

28. An enzyme-free diagnostic reagent for determining the presence of an entity to be assayed in a homogeneous assay comprising an enzyme-free hydrolytic catalyst coupled by a linking group to a first binding agent, said enzyme-free catalyst prior to being coupled to said first binding agent having a structure corresponding to a formula selected from the group consisting of

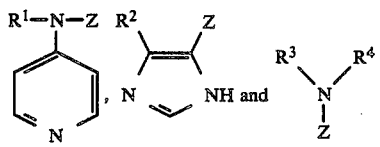

wherein $R^1$ is hydrogen, $C_1$-$C_{12}$ alkyl or Z, or $R^1$ and Z taken together form a 5- or 6-membered ring that contains a linking moiety;

$R^2$ is hydrogen or $C_1$-$C_4$ alkyl;

$R^3$ is $C_1$-$C_4$ alkyl, and $R^4$ is alkyl or substituted arylalkyl containing 1 to about 18 carbon atoms, or two of $R^3$, $R^4$ and Z taken together form a 5- or 6-membered ring containing a linking moiety, or $R^3$, $R^4$ and Z taken together form a bicyclic ring compound containing a linking moiety and wherein each of the rings of the bicyclic ring compound contains 5- or 6-membered ring that contains a linking moiety; and Z is a linking group including a linking moiety prior to linking of the catalyst to the first binding agent; said catalyst having a molecular weight together with the linking group of about 75 to about 2000 daltons, wherein said catalyst catalyzes a hydrolytic chemical reaction with successive preselected hydrolyzable co-reactant molecules when said co-reactant molecules and said catalyst are admixed in homogeneous solution and said catalyst is coupled to said first binding agent as said diagnostic reagent; said diagnostic reagent specifically binding in aqueous medium to a second binding moiety to form a binding complex, said second binding moiety being (a) the entity to be assayed in a direct assay, or (b) an entity needed for the assay in an indirect assay, said diagnostic reagent indicating the amount of said second binding moiety present in said binding complex by means of the catalytic reactivity of said catalyst with said co-reactant molecules, said catalytic reactivity being changed when said binding complex is formed.

29. The enzyme-free diagnostic reagent of claim 28 wherein said first binding agent is a ligand.

30. The enzyme-free diagnostic reagent of claim 28 wherein said first binding agent is a receptor.

31. The enzyme-free diagnostic reagent of claim 28 wherein said first binding agent includes avidin bound thereto.

32. The enzyme-free diagnostic reagent of claim 28 wherein said first binding agent comprises a polynucleic acid.

33. A diagnostic kit comprising at least one package containing an aqueous solution including a known amount of an enzyme-free diagnostic reagent for determining the presence of an entity to be assayed in a homogeneous assay, said diagnostic reagent comprising an enzyme-free hydrolytic catalyst coupled by a linking group to a first binding agent, said enzyme-free hydrolytic catalyst prior to being coupled to said first binding agent has a structure corresponding to a formula selected from the group consisting of

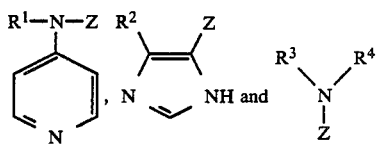

wherein $R^1$ is hydrogen, $C_1$-$C_{12}$ alkyl or Z, or $R^1$ and Z taken together form a 5- or 6- members;

$R^2$ is hydrogen or C-$C_4$ alkyl;

$R^3$ is $C_1$-$C_4$ alkyl, and $R^4$ is alkyl or substituted arylalkyl containing 1 to about 18 carbon atoms, or two of $R^3$, $R^4$ and Z taken together form a 5- or 6-membered ring containing a linking moiety, or $R^3$, $R^4$ and Z taken together form a bicyclic ring compound containing a linking moiety and wherein each of the rings of the bicyclic ring compounds contains 5- or 6-membered ring that contains a linking moiety; and Z is a linking group including a linking moiety prior to linking of the catalyst to the first binding agent; said catalyst having a molecular weight together with the linking group of about 75 to about 2000 daltons, wherein said catalyst catalyzes a hydrolytic chemical reaction with successive preselected hydrolyzable co-reactant molecules when said co-reactant molecules and said catalyst are admixed in homogeneous solution and said catalyst is coupled to said first binding agent as said diagnostic reagent; said diagnostic reagent specifically binding in aqueous medium to a second binding moiety to form a binding complex, said second binding moiety being (a) the entity to be assayed in a direct assay, or (b) an entity for the assay in an indirect assay, said diagnostic reagent indicating the amount of said second binding moiety present in said binding complex by means of the catalytic reactivity of said catalyst with said co-reactant molecules, said catalytic reactivity being changed when said binding complex is formed.

34. The diagnostic kit of claim 33 wherein said first binding agent is a ligand.

35. The diagnostic kit of claim 33 wherein said first binding agent is a receptor.

36. The diagnostic kit of claim 33 wherein said first binding agent includes avidin bound thereto.

37. The diagnostic kit of claim 33 wherein said first binding agent comprises a polynucleic acid.

38. A method of carrying out a binding assay comprising the steps of
(a) providing an enzyme-free diagnostic reagent for determining the presence of an entity to be assayed in a homogeneous assay comprising an enzyme-free hydrolytic catalyst coupled by a linking group to a first binding agent, said enzyme-free hydrolytic catalyst prior to being coupled to said first binding agent has a structure corresponding to a formula selected from the group consisting of

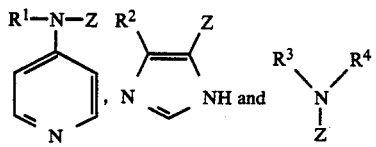

wherein $R^1$ is hydrogen, $C_1$-$C_{12}$ alkyl or Z, or $R^1$ and Z taken form a 5- or 6-membered ring that contains a linking moiety;

$R^2$ is hydrogen or $C_1$-$C_4$ alkyl;

$R^3$ is C-$C_4$ alkyl, and $R^4$ is alkyl or substituted arylalkyl containing 1 to about 18 carbon atoms, or two of $R^3$, $R^4$ and Z taken together form a 5- or 6-membered ring containing a linking moiety, or $R^3$, $R^4$ and Z taken together form a bicyclic ring compound containing a linking moiety and wherein each of the rings of the bicyclic ring compound contains 5- or 6-membered ring that contains a linking moiety; and Z is a linking group including a linking moiety prior to linking of the catalyst to the first binding agent. said cataylst having a molecular weight together with the linking group of about 75 to about 2000 daltons, wherein said catalyst catalyzes a hydrolytic chemical reaction with successive preselected hydrolyzable co-reactant molecules when said co-reactant molecules and said catalyst are admixed in homogeneous solution and said catalyst is coupled to said first binding agent as said diagnostic reagent; said diagnostic reagent specifically binding in aqueous medium to a second binding moiety to form a binding complex, said second binding moiety being (a) the entity to be assayed in a direct assay, or (b) an entity needed for the assay in an indirect assay, said diagnostic reagent indicating the amount of said second binding moiety present in said binding complex by means of the catalytic reactivity of said catalyst with said co-reactant molecules, said catalytic reactivity being changed when said binding complex is formed;

(b) providing a first aqueous composition containing said second binding moiety;

(c) admixing in an aqueous medium a known, predetermined amount of said diagnostic reagent and a known, predetermined amount of said first aqueous composition to form a binding complex between said diagnostic reagent and said second binding moiety;

(d) admixing a plurality of hydrolyzable co-reactant molecules with the admixture of step (c); and (e) measuring the reaction between said enzyme-free catalyst and said co-reactant molecules.

39. The method of claim 38 wherein said first binding agent is a ligand.

40. The method of claim 38 wherein said first binding agent is a receptor.

41. The method of claim 38 wherein said first binding agent includes avidin bound thereto.

42. The method of claim 38 wherein said first binding agent comprises a polynucleic acid.

* * * * *

UNITED STATES PATENT AND TRADEMARK OFFICE
CERTIFICATE OF CORRECTION

PATENT NO. : 4,719,176
DATED : January 12, 1988
INVENTOR(S) : Irving M. Klotz

It is certified that error appears in the above-identified patent and that said Letters Patent is hereby corrected as shown below:

Column 18, lines 67-68, delete "pyridyl-)" and insert --pyridyl)- --.

Claim 19, line 13, remove period after "admixed".

Claim 25, line 6, delete "sid" and insert --said--.

Claim 26, line 12, delete "regent" and insert --reagent--.

Claim 38, line 13, insert --together-- after "taken".

Claim 38, line 16, delete "C-$C_4$" and insert --$C_1$-$C_4$--.

Signed and Sealed this

Nineteenth Day of July, 1988

Attest:

DONALD J. QUIGG

*Attesting Officer*  *Commissioner of Patents and Trademarks*